US011707437B2

United States Patent
Premkumar et al.

(10) Patent No.: US 11,707,437 B2
(45) Date of Patent: Jul. 25, 2023

(54) TOPICAL FORMULATIONS WITH RESINIFERATOXIN NANOPARTICLES AND METHODS

(71) Applicants: Board of Trustees of Southern Illinois University, Springfield, IL (US); University of Wyoming, Laramie, WY (US)

(72) Inventors: Louis Premkumar, Springfield, IL (US); Baskaran Thyagarajan, Laramie, WY (US)

(73) Assignees: BOARD OF TRUSTEES OF SOUTHERN ILLINOIS UNIVERSITY, Springfield, IL (US); UNIVERSITY OF WYOMING, Laramie, WY (US)

( * ) Notice: Subject to any disclaimer, the term of this patent is extended or adjusted under 35 U.S.C. 154(b) by 175 days.

(21) Appl. No.: 16/925,551

(22) Filed: Jul. 10, 2020

(65) Prior Publication Data
US 2021/0007998 A1    Jan. 14, 2021

Related U.S. Application Data

(60) Provisional application No. 62/873,520, filed on Jul. 12, 2019.

(51) Int. Cl.
| | | |
|---|---|---|
| A61K 9/51 | (2006.01) |
| A61K 31/35 | (2006.01) |
| A61K 9/00 | (2006.01) |
| A61K 9/06 | (2006.01) |
| A61K 47/36 | (2006.01) |
| A61K 47/10 | (2017.01) |
| A61K 47/22 | (2006.01) |
| A61P 25/02 | (2006.01) |

(Continued)

(52) U.S. Cl.
CPC .......... *A61K 9/5153* (2013.01); *A61K 9/0014* (2013.01); *A61K 9/06* (2013.01); *A61K 9/7015* (2013.01); *A61K 31/35* (2013.01); *A61K 47/10* (2013.01); *A61K 47/22* (2013.01); *A61K 47/36* (2013.01); *A61K 47/44* (2013.01); *A61P 25/02* (2018.01)

(58) Field of Classification Search
None
See application file for complete search history.

(56) References Cited

U.S. PATENT DOCUMENTS 5,290,816 A    3/1994  Blumberg
9,173,940 B1   11/2015 Banov
(Continued)

OTHER PUBLICATIONS

Young et al. (Analgesic and anti-inflammatory activities of [6]-gingerol), Journal of Ethnopharmacology 96, 207-210 (Year: 2005).*

(Continued)

*Primary Examiner* — Isis A Ghali
(74) *Attorney, Agent, or Firm* — Greer, Burns & Crain, Ltd.

(57) ABSTRACT

Nanoparticles comprising resiniferatoxin (RTX) encapsulated in a poly(lactic-co-glycolic acid) (PLGA) polymer and compositions, especially topical compositions, comprising the nanoparticles. The compositions can be used as topical formulations for ameliorating pain, including for diabetic patients with peripheral neuropathy.

14 Claims, 7 Drawing Sheets

(51) Int. Cl.
A61K 9/70 (2006.01)
A61K 47/44 (2017.01)

(56) References Cited

U.S. PATENT DOCUMENTS

| | | | |
|---|---|---|---|
| 9,320,749 B2 | 4/2016 | Thyagarajan et al. | |
| 9,750,813 B2 | 9/2017 | Banov | |
| 9,775,872 B2 | 10/2017 | Banov | |
| 9,867,775 B2 | 1/2018 | Banov | |
| 9,913,908 B2 | 3/2018 | Simmons et al. | |
| 2013/0085171 A1 | 4/2013 | Ray, II et al. | |
| 2014/0079642 A1* | 3/2014 | Benita | A61K 31/573 424/179.1 |
| 2017/0042834 A1* | 2/2017 | Westphal | A61P 25/14 |
| 2020/0405657 A1* | 12/2020 | Small-Howard | G01N 33/946 |

OTHER PUBLICATIONS

Baskaran et al. "Preparation and evaluation of PLGA-coated capsaicin magnetic nanoparticles", Pharm. Res. (Year: 2017).*
Alleman CJM et al., Humanistic and Economic Burden of Painful Diabetic Peripheral Neuropathy in Europe: A Review of the Literature, Diabetes Research and Clinical Practice, 2015, pp. 215-225, vol. 109, No. 2.
Backonja M et al., NGX-4010, a High-Concentration Capsaicin Patch, for the Treatment of Postherpetic Neuralgia: a Randomised, Double-Blind Study, The Lancet Neurology, 2008, pp. 1106-1112, vol. 7, No. 12.
Baskaran M et al., Preparation and Evaluation of PLGA-Coated Capsaicin Magnetic Nanoparticles, Pharmaceutical Research, 2017, pp. 1255-1263, vol. 34, No. 6.
Bishnoi M et al., Preservation of Acute Pain and Efferent Functions Following Intrathecal Resiniferatoxin-Induced Analgesia in Rats, The Journal of Pain, 2011, pp. 991-1003, vol. 12, No. 9.
Bishnoi M et al., Streptozotocin-Induced Early Thermal Hyperalgesia is Independent of Glycemic State of Rats: Role of Transient Receptor Potential Vanilloid 1 (TRPVI) and Inflammatory Mediators, Molecular Pain, 2011, article No. 52, vol. 7.
Boulton AJM et al., Diabetic Somatic Neuropathies, Diabetes Care, 2004, pp. 1458-1486, vol. 27, No. 6.
Boulton AJM et al., Diabetic Neuropathies: a Statement by the American Diabetes Association, Diabetes Care, 2005, pp. 956-962, vol. 28, No. 4.
Bril V et al., Evidence-Based Guideline: Treatment of Painful Diabetic Neuropathy: Report of the American Academy of Neurology, the American Association of Neuromuscular and Electrodiagnostic Medicine, and the American Academy of Physical Medicine and Rehabilitation, Neurology, 2011, pp. 1758-1765, vol. 76, No. 20.
Bril V et al., ERRATUM: Evidence-Based Guideline: Treatment of Painful Diabetic Neuropathy: Report of the American Academy of Neurology, the American Association of Neuromuscular and Electrodiagnostic Medicine, and the American Academy of Physical Medicine and Rehabilitation, Neurology, 2011, p. 603, vol. 77, No. 6.
Brown DC et al., Intrathecal Resiniferatoxin in a Dog Model: Efficacy in Bone Cancer Pain, Pain, 2015, pp. 1018-1024, vol. 156, No. 6.
Brown JD et al., CT-Guided Injection of a TRPV1 Agonist Around Dorsal Root Ganglia Decreases Pain Transmission in Swine, Science Translational Medicine, 2015, article No. 305ra145, vol. 7, No. 305.
The Capsaicin Study Group, Treatment of Painful Diabetic Neuropathy with Topical Capsaicin. A Multicenter, Double-Blind, Vehicle-Controlled Study, Archives of Internal Medicine, 1991, pp. 2225-2229, vol. 151, No. 11.
Forst T et al., The Influence of Local Capsaicin Treatment on Small Nerve Fiber Function and Neurovascular Control in Symptomatic Diabetic Neuropathy, Acta Diabetologica, 2002, pp. 1-6, vol. 39, No. 1.

Gaskin DJ & RICHARD P, The Economic Costs of Pain in the United States, The Journal of Pain, 2012, pp. 715-724, vol. 13, No. 8.
Gavva NR et al., The Vanilloid Receptor TRPV1 is Tonically Activated in Vivo and Involved in Body Temperature Regulation, The Journal of Neuroscience, 2007, pp. 3366-3374, vol. 27, No. 13.
Gavva NR et al., Pharmacological Blockade of the Vanilloid Receptor TRPV1 Elicits Marked Hyperthermia in Humans, Pain, 2008, pp. 202-210, vol. 136, No. 1-2.
Haanpaa M et al., Capsaicin 8% Patch Versus Oral Pregabalin in Patients with Peripheral Neuropathic Pain, European Journal of Pain, 2016, pp. 316-328, vol. 20, No. 2.
Iadorola MJ & Mannes AJ, The Vanilloid Agonist Resiniferatoxin for Interventional-Based Pain Control, Current Topics in Medicinal Chemistry, 2011, pp. 2171-2179, vol. 11, No. 17.
Iadarola MJ & Gonnella GL, Resiniferatoxin for Pain Treatment: An Interventional Approach to Personalized Pain Medicine, The Open Pain Journal, 2013, pp. 95-107, vol. 6, No. 1.
Irving GA et al., A Multicenter, Randomized, Double-Blind, Controlled Study of NGX-4010, a High-Concentration Capsaicin Patch, for the Treatment of Postherpetic Neuralgia, Pain Medicine, 2011, pp. 99-109, vol. 12, No. 1.
Jain RA, The Manufacturing Techniques of Various Drug Loaded Biodegradable Poly(lactide-co-glycolide) (PLGA) Devices, Biomaterials, 2000, pp. 2475-2490, vol. 21, No. 23.
Jeffry JA et al., Selective Targeting of TRPV1 Expressing Sensory Nerve Terminals in the Spinal Cord for Long Lasting Analgesia, PLoS One, 2009, article No. e7021, vol. 4, No. 9.
McCall B, Capsaicin Patch Approved in EU for Diabetic Neuropathy Pain, www.medscape.com, 2015, available at www.medscape.com/viewarticle/851245_print.
Mitchell K et al., Ablation of Rat TRPV1-Expressing Adelta/C-Fibers with Resiniferatoxin: Analysis of Withdrawal Behaviors, Recovery of Function and Molecular Correlates, Molecular Pain, 2010, article No. 94, vol. 6.
Mitchell K et al., Nociception and Inflammatory Hyperalgesia Evaluated in Rodents Using Infrared Laser Stimulation After Trpv1 Gene Knockout or Resiniferatoxin Lesion, Pain, 2014, pp. 733-745, vol. 155, No. 4.
Pabbidi RM et al., Influence of TRPV1 on Diabetes-Induced Alterations in Thermal Pain Sensitivity, Molecular Pain, 2008, article No. 9, vol. 4.
Pabbidi RM et al., Direct Role of Streptozotocin in Inducing Thermal Hyperalgesia by Enhanced Expression of Transient Receptor Potential Vanilloid 1 in Sensory Neurons, Molecular Pharmacology, 2008, pp. 995-1004, vol. 73, No. 3.
Panyam J et al., Rapid Endo-Lysosomal Escape of Poly(DL-lactide-co-glycolide) Nanoparticles: Implications for Drug and Gene Delivery, FASEB Journal, 2002, pp. 1217-1226, vol. 16, No. 10.
Premkumar LS & Ahern GP, Induction of Vanilloid Receptor Channel Activity by Protein Kinase C, Nature, 2000, pp. 985-990, vol. 408, No. 6815.
Raisinghani M et al., Activation of Transient Receptor Potential Vanilloid 1 (TRPV1) by Resiniferatoxin, The Journal of Physiology, 2005, pp. 771-786, vol. 567, No. 3.
Salas MM et al., Local Resiniferatoxin Induces Long-Lasting Analgesia in a Rat Model of Full Thickness Thermal Injury, Pain Medicine, 2017, pp. 2453-2465, vol. 18, No. 12.
Simpson DM et al., Controlled Trial of High-Concentration Capsaicin Patch for Treatment of Painful HIV Neuropathy, Neurology, 2008, pp. 2305-2313, vol. 70, No. 24.
Simpson DM et al., Capsaicin 8% Patch in Painful Diabetic Peripheral Neuropathy: a Randomised, Double-Blind, Placebo-Controlled Study, The Journal of Pain, 2017, pp. 42-53, vol. 18, No. 1.
Szallasi A & Blumberg PM, Resiniferatoxin, a Phorbol-Related Diterpene, Acts as an Ultrapotent Analogue of Capsaicin, the Irritant Constituent in Red Pepper, Neuroscience, 1989, pp. 515-520, vol. 30, No. 2.
Tavakoli M et al., Review: Novel Insights on Diagnosis, Cause and Treatment of Diabetic Neuropathy: Focus on Painful Diabetic Neuropathy, Therapeutic Advances in Endocrinology and Metabolism, 2010, pp. 69-88, vol. 1, No. 2.

(56) References Cited

OTHER PUBLICATIONS

Tesfaye S et al., Diabetic Neuropathies: Update on Definitions, Diagnostic Criteria, Estimation of Severity, and Treatments, Diabetes Care, 2010, pp. 2285-2293, vol. 33, No. 10.
Tesfaye S et al., ERRATUM: Diabetic Neuropathies: Update on Definitions, Diagnostic Criteria, Estimation of Severity, and Treatments, Diabetes Care, 2010, p. 2725, vol. 33, No. 12.
Van Nooten F et al., Capsaicin 8% Patch Versus Oral Neuropathic Pain Medications for the Treatment of Painful Diabetic Peripheral Neuropathy: A Systematic Literature Review and Network Meta-Analysis, Clinical Therapeutics, 2017, pp. 787-803, vol. 39, No. 4.
Veves A et al., Painful Diabetic Neuropathy: Epidemiology, Natural History, Early Diagnosis, and Treatment Options, Pain Medicine, 2008, pp. 660-674, vol. 9, No. 6.
Yu S-Q & Premkumar LS, Ablation and Regeneration of Peripheral and Central TRPV1 Expressing Nerve Terminals and the Consequence of Nociception, The Open Pain Journal, 2015, pp. 1-9, vol. 8.
Rezvantalab et al., "PLAG-Based Nanoparticles in Cancer Treatment", Frontiers in Pharmacology, Nov. 2, 2018, pp. 1-19, vol. 9.

\* cited by examiner

TOPICAL FORMULATIONS WITH RESINIFERATOXIN NANOPARTICLES AND METHODS

CROSS-REFERENCE TO RELATED APPLICATIONS

This application claims the benefit of priority from U.S. provisional patent application 62/873,520 filed Jul. 12, 2019, the entire disclosure of which is herein incorporated by reference.

GOVERNMENT RIGHTS

This invention was made with government support under grant number DK117674 awarded by the National Institutes of Health. The government has certain rights in the invention.

TECHNICAL FIELD

The present disclosure relates to topical compositions and methods for treatment and management of pain and/or inflammation, including topical formulations which comprise PLGA-coated resiniferatoxin nanoparticles helpful in treating and/or managing diabetic peripheral neuropathy.

BACKGROUND

Diabetic Peripheral Neuropathy (DPN) is a common long-term complication of diabetes. DPN develops as a result of progressive loss of nerve fibers and can affect the somatic peripheral and autonomic nervous systems (2-4) DPN is associated with pain referred to as Painful Diabetic Peripheral Neuropathy (PDPN) in 10% to 20% of patients with diabetes and in 40% to 50% of those with diabetic neuropathies (5-7). Symptoms of PDPN include electrical or stabbing sensations, paresthesias, hyperesthesias, burning pain, pins and needles and deep aching pain (3,4) that can affect quality of life leading to anxiety, depression and sleep disturbances (8).

The symptoms of this debilitating condition begin with a feeling that resembles pins and needles accompanied by pain that later develops into numbness, parasthesia and ulceration in the extremities. Symptoms can be categorized as painful (positive symptoms) or painless (negative symptoms). 40-50% patients with DPN develop painful neuropathy and virtually all of them suffer from spontaneous and burning pain. The burning spontaneous pain and mechanical allodynia associated with DPN is correlated with spontaneous C fiber activity in almost all patients. If the condition is left untreated at the peripheral source, it may lead to central sensitization that includes the spinal cord and higher brain structures.

The main manifestations of painful DPN are persistent or shooting and burning spontaneous pain that affects virtually every patient and mechanical allodynia that affects up to 18% of patients. It has been shown in DPN patients and STZ rodents that the number of spontaneously active nociceptive fibers is drastically increased compared to healthy subjects and untreated rodents. It has also been shown that block of nociceptive transmission from the periphery led to substantial improvement in pain scores. On the other hand, it has also been demonstrated that sensory deficit and denervation in DPN patients are not directly correlated with neuropathic pain. Therefore, it is expected that spontaneous neuropathic pain and mechanical allodynia are caused by spontaneously active primary C fibers. Majority of these fibers are TRPV1 positive subepidermal mechano-insensitive C fibers in DPN patients and STZ-induced diabetic animals. The subepidermal terminals of these fibers may be accessed only by single fiber recording because their thermal threshold is higher as compared to intraepidermal C fibers.

Several mechanisms have been proposed for the neuronal damage and gain/loss of function in DPN. These include a) oxidative and nitrative stress including activation of poly (ADP-ribose) polymerase (PARP); b) hyperglycemia leading to excessive polyol pathway flux, sorbitol accumulation and increased intracellular fructose, c) production of endogenous chemicals e.g. methylglyoxal (MG) that can covalently link to cellular proteins and DNA with d) consequent increase in production of advanced glycation end-products (AGEs), that can e) bind to a receptor (RAGE) and cause alterations in downstream signaling (including p38MAPK, NFκB and PKCβII).

These pathways affect microvascular tone leading to neuronal hypoxia. Sensory nerve endings express ion channels that respond to thermal, mechanical, and chemical stimuli, which include acid sensitive ion channels (ASIC), degenerin/epithelial sodium channels (DEG/ENAC), ATP-gated ion channels (P2X), transient receptor potential (TRP) channels, and piezo channels. Transient receptor potential vanilloid 1 (TRPV1), a nonselective cation channel with high calcium permeability is expressed on the peripheral and the central terminals of small diameter sensory neurons. Enhanced TRPV1 expression in the central terminals of sensory neurons release neuropeptides (CGRP and SP) can activate glia and increase synthesis and release of inflammatory mediators.

Transient Receptor Potential Vanilloid 1 (TRPV1) receptor is involved in inflammatory thermal hyperalgesia and plays a significant role in PDPN. Capsaicin, a TRPV1 agonist, applied topically has been shown to relieve pain and improve sensory perception in humans with DPN (Capsaicin Study group., 1991; 9, 10). Similarly, TRPV1 antagonists can be effective in treating painful conditions. Unfortunately, in clinical trials it became apparent that TRPV1 antagonists, although showed excellent analgesia, but caused sustained hyperthermia (11,12). It has been shown using a transgenic mouse model of diabetes and STZ-induced diabetes that TRPV1 expression and function are increased and decreased in hyper or hypoalgesic phenotypes, respectively (13).

Resiniferatoxin (abbreviated as RTX, CAS Number 57444-62-9) is an ultrapotent TRPV1 agonist. RTX fully activates TRPV1 receptor at very low concentrations (femtomolar-picomolar range). The ultra-potency of RTX was demonstrated by recording TRPV1-mediated membrane currents using patch-clamp techniques (13-16). RTX is a well-tolerated drug which can be administered at concentrations as high as 200 µg/kg intraperitoneally in rats without observable side effects using common techniques to test toxicity over a period of 9 months (17,19).

The role of TRPV1 in painful conditions has been confirmed in studies by administration of RTX, which reversed inflammatory thermal pain in conditions including PDPN (15-23). Furthermore, it has been demonstrated by diode laser fiber type selective stimulation (DLss) of AA and C fibers that depletion of TRPV1 positive peripheral terminals by local intra-dermal administration of RTX led to complete loss of pain sensitivity in rodents (24,25). Intrathecal administration of RTX is being tested in a clinical trial for certain terminal cancer pain conditions (26,27) (NCT00804154).

Oral formulations of TRPV1 agonists are suggested, including those disclosed in U.S. Pat. No. 9,320,749.

Certain localized and topical treatments are treatment options for painful conditions are also available (28). Examples of localized treatments include a high dose of capsaicin 179 mg (8% transdermal patch; ~250 mM) cutaneous patch which provides effective durable pain relief from single application in patients with peripheral neuropathic pain (29-31). In a direct comparison, 8% capsaicin patch has been shown to be noninferior to pregabalin in the control of neuropathic pain but has a faster onset of analgesia with fewer systemic side effects. (32,33). However, topical application of capsaicin can be painful, particularly for treatments containing the relatively high capsaicin concentrations necessary to deliver an effective dose. Furthermore, 8% capsaicin has significant adverse effects in some patients that include severe pain during localized application, erythema and pruritis. Thus, there remains the need in the field for topical formulations with TRPV1 agonists/antagonists, in which the side effects are minimized.

There also remains the need in the art for topical formulations with RTX in which a delivery of RTX through the transdermal barrier is sufficiently efficient in order for RTX to act rapidly to alleviate pain in patients with Diabetic Peripheral Neuropathy and other patients in need of pain management and/or inflammation treatment.

SUMMARY

The present disclosure provides topical formulations containing extremely low, yet therapeutically effective doses of RTX. These formulations can be topically applied to treat DPN or other conditions in which pain and/or inflammation must be managed, without causing pain at the application site. In some embodiments, the present disclosure provides a cream (and method of preparing said cream) that contains concentrations of RTX ranging from 100 femtomolar (fM) to one micromolar (μM). Preferred formulations comprise PLGA-coated RTX nanoparticles ($_{PLGA}RTX^{NANO}$), which enhance the bioavailability of RTX.

In one aspect, the present disclosure provides a nanoparticle comprising resiniferatoxin (RTX) encapsulated in a poly(lactic-co-glycolic acid) (PLGA) polymer.

In another aspect, the present disclosure provides a composition comprising nanoparticles in which resiniferatoxin is encapsulated in a poly(lactic-co-glycolic acid) (PLGA) polymer, and wherein the composition comprises one or more excipients. Some of the compositions comprise the nanoparticles in an amount from 0.001% to 99% by weight, based on the total weight of the composition.

Some of the nanoparticles or the compositions include those, wherein the ratio of lactic acid to glycolic acid is 25/75; 50/50; 75/25; or 100/0 in the PLGA polymer.

The nanoparticles may have a molecular weight in the range from 1 kDa to 200 kDa.

The nanoparticles may be between 1 and 200 nanometers in size.

In some embodiments, the nanoparticles and the compositions with the nanoparticles include a concentration of resiniferatoxin in the range from 100 femtomolar (fM) to one micromolar (μM) per one liter.

Some embodiments include the nanoparticles and/or the compositions, wherein a concentration of resiniferatoxin is in the range from 0.1 nanomoles (nM) to 10 nM per one liter.

Some embodiments include the nanoparticles and/or the compositions, wherein a concentration of resiniferatoxin is in the range from 10 nM to 100 nM per one liter.

Some embodiments include the nanoparticles and/or the compositions, wherein the nanoparticles are PEGylated.

Some embodiments include the nanoparticles and/or the compositions, wherein the nanoparticles further comprise one or more of the following: an anti-inflammatory drug, an antibiotic, an anti-viral drug, an anti-fungal drug, a vitamin or an analgesic.

Some embodiments include the compositions, wherein the compositions further comprise one or more of the following: an anti-inflammatory drug, an antibiotic, an anti-viral drug, an anti-fungal drug, vitamin E, vitamin D or an analgesic.

Some embodiments include the compositions, wherein the compositions comprise from 0.01% w/w to 95% w/w of the PLGA-coated RTX nanoparticles, based on the total weight of the composition.

Some embodiments include the compositions, wherein the compositions comprise from 0.1% w/w to 50% of the PLGA-coated RTX nanoparticles.

Some of the disclosed compositions are topical compositions.

Some of the disclosed compositions include the compositions in a form of a cream, ointment, liniment, lotion, gel, collodion, paste, patch, tape, solution, spray, foam or an injectable solution.

Any of the topical compositions of this disclosure may comprise one or more of the following excipients: water, oils, synthetic oils, vegetable oils, animal oils, fatty acids and/or their esters and/or their salts, glycols, polyethylene, polyethylene glycol and/or its derivatives, alcohols, vitamins, vitamin E, vitamin D, glycerol and/or its derivatives, ethanol, propanol, resins, parabens, petrolatum, polysorbates, polyisobutylene, alginate, starch and its derivatives, talc, oxidized cellulose, methyl-cellulose, caraboxymethyl cellulose, paraffin, kaolin, agar, dextran and its derivatives, pectin, gelatin, collagen, guar gum, xanthan gum, chalk, polycarbonates, polysaccharides, salts and/or oxides of one or more of the following: calcium, aluminum, sodium, magnesium, zinc and/or potassium.

Any of the topical compositions of this disclosure may comprise alcohol, polyethylene glycol (PEG), glycerin, lecithin, shea butter, coconut oil, ascorbyl palmitate, xanthan gum and/or disodium ethylenediaminetetraacetic acid (EDTA). The alcohol may be cetearyl alcohol.

The compositions of this disclosure may further comprise a nonsteroidal anti-inflammatory drug and/or vitamin E and/or vitamin D.

In further aspect, the present disclosure provides a method of treating a subject in need of pain management, the method comprising applying to the subject's skin with the topical compositions according to this disclosure.

Some of these methods include those, wherein resiniferatoxin is applied in an amount form 1 nM to 100 nM RTX per one application.

Some of the present methods include those, wherein the subject is a diabetic patient whose symptoms include diabetic peripheral neuropathy.

Some of the present methods include those, wherein the subject is a patient afflicted with at least one of the following diseases and/or conditions: peripheral neuropathy, diabetic peripheral neuropathy, herpes, shingles, arthritis, osteoarthritis, rheumatoid arthritis, swollen joints, muscle pain, muscle sourness, muscle stiffness, muscle crumps, insect bites, skin injuries, skin burns, back pain, elbow pain, knee pain, low back pain, shoulder tension, or joint injuries.

In further aspect, the present disclosure provides a method of treating diabetic peripheral neuropathy, the method comprising applying any of the topical compositions of this disclosure to a skin area. In some of these treatment methods, the composition is applied at least once a month. In some other of these treatment methods, the composition is applied at least once a week.

In yet another aspect, the present disclosure provides a method for making the nanoparticles according to this disclosure, the method comprises:
a) dissolving resiniferatoxin in a first solvent and obtaining a first solution, wherein the first solvent is water-miscible;
b) dissolving a poly(lactic-co-glycolic acid) (PLGA) polymer powder in a second solvent, and obtaining a second solution;
c) mixing the first solution together with the second solution, and obtaining a mixture;
d) adding the mixture dropwise to an aqueous solution with mixing, and thereby forming the nanoparticles; and
e) collecting the nanoparticles by one or more of centrifugation and/or filtration.

Some of these methods include those, wherein a concentration of the resiniferatoxin in the first solution is in the range from 1 fM per liter to 10 μM per liter.

Some of these methods include those, wherein the first solvent contains ethanol.

Some of these methods include those, wherein the second solvent contains dichloromethane. Some of these methods include those, wherein from 0.001 to 2 parts by weight of resiniferatoxin can be used for 100 parts by weight of the PLGA powder.

In further aspect, the present disclosure provides a method for alleviating pain in a patient with a skin burn, the method comprising: applying any of the present compositions over the skin burn. In one preferred embodiment of the method, the composition is applied as a cream or spray.

DETAILED DESCRIPTION

In one aspect, the present disclosure provides nanoparticles in which resiniferatoxin is encapsulated in a PLGA coating, these nanoparticles may be referred in this disclosure as $_{PLGA}RTX^{NANO}$ nanoparticles or as PLGA-coated RTX nanoparticles interchangeably. The PLGA-coated RTX nanoparticles provide a gradual and consistent release of resiniferatoxin and reduce the burst release of resiniferatoxin. In another aspect, the present disclosure provides compositions which comprise the PLGA-coated RTX nanoparticles.

Resiniferatoxin is a benzeneacetate derivative with formula C37H4009, molecular weight 628.72 and CAS Number 57444-62-9. Resiniferatoxin is abbreviated in this disclosure as RTX. Resiniferatoxin is commercially available from different companies, including Tocris (Bristol, UK).

Poly(lactic-co-glycolic acid) polyester, abbreviated as PLGA, is an FDA approved copolymer which is biodegradable and bioabsorbable. PLGA has numerous advantages in drug delivery. It is a biodegradable and biocompatible polymer approved by the US FDA for use in humans. PLGA co-polymers are metabolized in the body by the hydrolytic cleavage of the ester linkage to produce lactic acid and glycolic acid. The monomers are metabolized via Kreb's cycle producing carbon dioxide and water.

Different forms of PLGA are known, depending on the molar ratios of lactic acid (LA) to glycolic acid (GA) monomers being used. A rate of release of RTX from the nanoparticles can be controlled by using PLGA with the appropriate LA/GA ratio. Typically, PLGA with a ratio of lactic acid monomers to glycolic acid monomers in the range from 75:25 to 25:75, with the preference for the 50:50 ratio, can be used. If a faster rate of degradation is need, the proportion of glycolic acid monomers in the co-polymer can be increased. Suitable PLGA co-polymers according to this disclosure may be end-capped. The molecular weight of the nanoparticles may be also controlled as may be needed. Suitable PLGA-coated RTX nanoparticles include nanoparticles with the following LA/GA ratios: 25/75; 50/50; 75/25; or 100/0.

Suitable nanoparticles may be of different molecular weight. The higher is the molecular weight of the nanoparticles, the slower is the rate of RTX release. In some embodiments, the nanoparticles have a molecular weight in the range from about 1 kDa to about 200 kDa, and preferably from 5 kDa to 100 kDa.

The PLGA-coated RTX nanoparticles may be prepared in different shapes, including as spheres, rods and/or needles, depending on the application and a manufacturing method. In a preferred embodiment, the PLGA-coated RTX nanoparticles are spheres.

The $_{PLGA}RTX^{NANO}$ nanoparticles may be made in different sizes. In one preferred embodiment, the PLGA-coated RTX nanoparticles are between 1 and 200 nanometers (nm) in size, and more preferably between 5 nm and 100 nm in size.

In some embodiments, the PLGA coating may further comprise other ingredients, e.g. moieties co-polymerized in the PLGA co-polymer and/or other compounds which may aid in improving penetration of the nanoparticles through the transdermal barrier and/or in controlling the biodegradation rate of the PLGA coating and the RTX release from the nanoparticles. The $_{PLGA}RTX^{NANO}$ nanoparticles may further comprise one or more chemical moieties displayed at the surface of the nanoparticle. Suitable moieties include, but are not limited to, peptides, antibodies, aptamers and/or other biomolecules and/or other chemical moieties, e.g. chitosan or PEG, displayed at the surface of the PLGA coating. These moieties may aid in delivering the nanoparticles through the transdermal barrier of skin. In some embodiments, the $_{PLGA}$RTX$^{NANO}$ nanoparticles may be PEGylated and display PEG (polyethylene glycol) and/or chitosan at the surface.

In some embodiments for the $_{PLGA}$RTX$^{NANO}$ nanoparticles, RTX may be conjugated to a carrier, such for example as certain metal compounds, including metal salts such as for example as iron, nickel or cobalt-based salts.

The PLGA-coated RTX nanoparticles may be loaded with different amounts of resiniferatoxin. Any therapeutically effective amount of RTX can be used.

By a "therapeutically effective amount," it is meant in this disclosure any amount of RTX effective in ameliorating at least partially at least some of the pain symptoms, as reported by a subject who is applying a composition comprising the nanoparticles to his/her skin.

In some embodiments, a concentration of RTX in the nanoparticles is in the range from 100 femtomoles (fM) to one micromole (μM) per one liter, and preferably from 0.1 nanomoles (nM) to 10 nM per one liter, and more preferably from 0.3 nM to 5 nM per one liter.

One of the technical advantages of the present compositions which comprise the PLGA-coated RTX nanoparticles is that the nanoparticles deliver efficiently through the transdermal barrier RTX in low concentrations, including concentrations of RTX ranging from 100 femtomolar (fM) to one micromolar (μM).

In the PLGA-coated RTX nanoparticles, RTX is an active ingredient used for treating pain.

The term "treatment" means in this disclosure ameliorating (alleviating or relieving) pain at least partially and at least for a period of time, e.g. 1 to 4 hours. The term "ameliorating" means decreasing at least temporary and/or at least partially. The decrease in pain may be determined, based on as reported by a patient who is applying a composition comprising the PLGA-coated RTX nanoparticles to his/her skin and reports the level of his/her pain sensation before the application and after the application.

In some embodiments, the PLGA-coated RTX nanoparticles may comprise some other active ingredients in addition to RTX. Such ingredients may include one or more of the following: an anti-inflammatory drug, an antibiotic, an anti-viral drug, an anti-fungal drug, a vitamin, an analgesic and/or some other compounds which may provide additional treatments simultaneously with management of pain, as provided by RTX.

The present compositions comprising the PLGA-coated RTX nanoparticles may comprise one or more excipients. Suitable excipients include solvents, surfactants, stabilizers and fillers. One of the preferred excipients is water. The present compositions may further comprise other active ingredients in addition to the PLGA-coated RTX nanoparticles. Such other active ingredient may include, but are not limited to, an anti-inflammatory drug, an antibiotic, an anti-viral drug, an anti-fungal drug, an analgesic, a vitamin, vitamin E, vitamin D, and/or some other compounds. In preferred embodiments, the additional active ingredient is an anti-inflammatory drug which may be a non-steroidal anti-inflammatory drug (NSAID) and/or a vitamin, preferably vitamin E and/or vitamin D.

In some embodiments, the present compositions comprise from 0.001% w/w to 100% w/w of the PLGA-coated RTX nanoparticles. Preferably, the present compositions comprise from 0.01% w/w to 95% w/w of the PLGA-coated RTX nanoparticles. More preferably, the topical formulations comprise from 0.1% w/w to 50% of the PLGA-coated RTX nanoparticles.

In the present disclosure "w/w" means by weight from the total weight of the composition, e.g. 100 g of the topical formulation may comprise from 0.001 g (0.001% w/w) to 100 g (100% w/w) of the PLGA-coated RTX nanoparticles.

Preferred compositions of this disclosure are topical formulations which are applied over subject's skin. The most preferred compositions of this disclosure are topical compositions which are transdermal formulations/compositions. The term "transdermal formulation or composition" means that the composition permeates through the stratum corneum of skin. The inventors have discovered that the compositions comprising the PLGA-coated RTX nanoparticles possess transdermal properties. Thus, the PLGA-coating facilitates delivery of RTX through the stratum corneum and to the nerve endings.

In a further embodiment, the present disclosure provides topical formulations/compositions which comprise the PLGA-coated RTX nanoparticles. The topical compositions may be prepared in a form of a cream (emulsified ointment), ointment, liniment (a topical emulsion), lotion (a topical suspension), gel, collodion, paste, patch, tape, solution, spray, foam, or any other form suitable for a topical application over subject's skin. In some embodiments, the formulations may be formulated as an injectable solution. The formulations may be packaged with a dispenser which meters the amount of the topical formulation dispensed per one application. The amount of the PLGA-coated RTX nanoparticles to be used per one application depends on many different factors, e.g. the size of the affected area, patient's individual response to pain and other symptoms and conditions. In some preferred embodiments, from 1 nM to 10 nM RXT per application can be used.

One of the technical advantages of the present topical formulations comprising PLGA-coated RTX nanoparticles, is extremely low concentrations (femtomolar, fM) of RTX are shown to be effective in activating the transient receptor potential vanilloid 1 (TRPV1) channels associated with the hyperalgesic state of diabetic peripheral neuropathy (DPN). Unlike alternative active ingredients, such as capsaicin, that can cause pain upon application, RTX induces a depolarization block of the nerve terminals in the short-term and nerve terminal desensitization/ablation in the long-term of TRPV1 expressing nerve terminals, effectively eliminating short-term pain while preserving long-lasting pain relief characteristics.

The topical compositions comprising the PLGA-coated RTX nanoparticles of this disclosure do not induce pain during application, yet induce the desired effect such as pain management, by sustained activation of TRPV1 in the short-term and reversible depletion of nerve terminals in the longer-term.

Examples of localized treatments currently available on the market include a high dose of capsaicin 179 mg (8% transdermal patch; ~250 mM) cutaneous patch which provides effective durable pain relief from single application in patients with peripheral neuropathic pain However, 8% capsaicin has significant adverse effects in some patients that include severe pain during localized application, erythema and pruritus. The present topical formulations provided in this disclosure have a significant advantage of not inducing any of the adverse effect of capsaicin. A very low concentration (~6.28 ng; $6.28 \times 10^{-7}$% per application or 1 nM) of RTX has a desired effect for pain management without the need to combine with lidocaine or other active ingredients which may be used in the capsaicin applications.

The amount of RTX in the PLGA-coated nanoparticles and corresponding topical compositions may vary, depending on the application and the composition. Preferably, the topical compositions comprise a low amount of RTX, which as discussed above is present as the PLGA-coated RTX nanoparticles. In preferred embodiments, the topical compositions have concentrations equivalent to 0.1 nM to 1 uM of RTX, and more preferably the concentrations are equivalent to 0.1 nM to 10 nM of RTX.

The topical compositions may further comprise one or more of excipients. A particular selection of excipients depends on a form, e.g. cream versus a solution or a patch. Examples of suitable excipients include, but not limited to, solvents, stabilizers, dispersants, thickeners, coloring agents, surfactants, and preservatives.

Examples of suitable excipients include, but are not limited to, water, oils, synthetic oils, vegetable oils, animal oils, fatty acids and/or their esters and/or their salts, glycols, polyethylene, polyethylene glycol and/or its derivatives, alcohols, menthol, camphor, glycerol and/or its derivatives, ethanol, propanol, resins, parabens, petrolatum, polysorbates, polyisobutylene, alginate, starch and its derivatives, talc, oxidized cellulose, methyl-cellulose, caraboxymethyl cellulose, paraffin, kaolin, agar, dextran and its derivatives, pectin, gelatin, collagen, guar gum, xanthan gum, chalk, polycarbonates, polysaccharides, salts and/or oxides of one or more of the following: calcium, aluminum, sodium, magnesium, zinc and/or potassium. The salts include, but are not limited to, chloride, citrate, gluconate, lactate, and/or carbonate.

Commercially available bases for topical compositions can be also used. One particularly preferred transdermal cream base is the cream base composition disclosed in US patent publication US 20130085171 under the trade name Lipoderm ActiveMax™. As stated in US 20130085171, the entire disclosure of which is herein incorporated by reference, the Lipoderm ActiveMax™ cream base comprises water, alcohol (preferably, cetearyl alcohol), polyethylene glycol (PEG), glycerin, lecithin, shea butter, coconut oil, ascorbyl palmitate, xanthan gum and disodium ethylenediaminetetraacetic acid (EDTA).

In another aspect, the present disclosure provides methods for treating a subject in need of managing his/her pain. The subject may be a patient afflicted with at least one of the following diseases and/or conditions: peripheral neuropathy, including diabetic peripheral neuropathy (DPN), herpes, shingles, arthritis, osteoarthritis, rheumatoid arthritis, swollen joints, muscle pain, muscle sourness, muscle stiffness, muscle crumps, insect bites, skin injuries (burns, cuts, etc.), back pain (low back pain, back pain between shoulders, etc.), knee pain, elbow pain, shoulder tension, joint injuries and other conditions where a subject is afflicted with localized pain which can be addressed by a topical application of pain analgesic.

The present compositions, especially when formulated as a cream or spray, may be very effective in burn patients as application of RTX is likely to eliminate nerve terminals and the intense pain can be relieved. Over time, the terminals and the skin cells will regenerate.

The methods of treatment comprise applying one or more times, e.g. one to six times daily, any of the present compositions to the subject's skin over the area(s) where the subject experiences pain. As is shown in the present application, the compositions of this disclosure can be used for the same pain management indications for which capsaicin can be used.

Preferred methods of treatment for DPN include applying the topical composition comprising PLGA-coated RTX nanoparticles of this disclosure to the affected skin area with a preferred application frequency of once per week or even once a month, depending on the patient's condition.

Referring to FIG. 1, a typical dose response curve of capsaicin is shown, where the response curve is constructed using current recordings using patch clamp techniques from HEK cells heterologously and stably expressing TRPV1 ion channel. The EC50 is 109.36 nM for capsaicin in membrane current measurements. The FIG. 1 inset shows traces of current recording with increasing doses of capsaicin.

FIG. 2 reproduces the FIG. 1 capsaicin data and dose response curve for reference on an expanded X axis, but also includes data points for RTX at fM to pM concentrations. RTX is shown to activate TRPV1 ion channels (and generate a normalized current) when present in concentrations five to nine orders of magnitude lower than capsaicin, indicating a much higher potency of RTX batches as compared to capsaicin. Construction of a standard dose response curve for RTX is complicated by the fact that the maximal response attained is time dependent but not dose dependent.

Because RTX current amplitude is not a dose response, but is activation time dependent, a time response curve can be constructed to show the time to reach the peak vs concentration, as shown in FIG. 3.

The FIG. 3 data were generated by applying capsaicin (100 nM) to elicit a response which could be reversed by washout. However, when RTX was applied in a concentration of 7.9 fM, the current activated over time and could not be reversed by washout. Different concentrations of RTX Batch 1 (7.9 fM to 15.8 pM) applied following application of 100 nM capsaicin activated currents maximally but the rate of activation was concentration dependent (shown by the linear fits). Y axis is current amplitude and X-axis is time indicated by a 2 min bar.

These results suggest that RTX action cannot be compared to any other agonist that has been reported in the literature for treating DPN. RTX binds to the receptor irreversibly since the current cannot be reversed by washout even at very low concentrations, whereas the capsaicin and other agonists are susceptible to washout. This property that is unique to RTX allows for ultra-low doses (or concentrations) of RTX while achieving a maximal response against pain. When PLGA-coated RTX nanoparticles are applied in a cream form, RTX does not fire an action potential because of slow depolarization and the sodium channels cannot be activated in a concerted fashion leading to depolarization block. Capsaicin, on the other hand, when applied in ultra-low concentrations will not activate the sodium channels and there will not be any effect. But at effective concentrations of capsaicin, invariably an action potential will be triggered causing a painful sensation while applying. This painful sensation is avoided when using RTX at ultra-low doses and concentrations.

FIG. 4A shows experimental results following application of 10 nM RTX nanoparticle cream formulation to the plantar surface of the rat paw in diabetic female and male rats. FIG. 4B shows experimental results following application of 10 nM RTX nanoparticle cream formulation to the plantar surface of the rat paw in control female and male rats.

Thermal sensitivity was measured using Hargreaves method (sensitivity to radiant heat). The paw withdrawal latency was significantly decreased in diabetic animals reflecting diabetes induced thermal hyperalgesia. Treatment with RTX cream (Resinizin) readily reversed the enhanced thermal sensitivity. ** represents $P>0.05$.

FIG. 4C shows experimental results following application of 10 nM RTX nanoparticle cream formulation to the upper thigh regions in diabetic pigs. The side of the pig skin treated with RTX cream showed significantly lower sensitivity (lack of muscle twitch and trail twirling) to a thermal stimulus applied using diode laser source reflecting decreased thermal pain sensitivity. * represents P>0.05.

The above data indicate that the low-concentration $_{PLGA}RTX^{NANO}$ composition described in the present application may be applied on a weekly to monthly basis for the treatment of DPN, with a preferred application frequency of once per week.

It has been shown that altered expression of TRP channels synthesized in cell bodies tend to be transported to peripheral terminals (the "business end" of the neuron). For patients with DPN, enhanced neuronal activity from the periphery is expected to result in higher TRPV1 expression and function in the spinal cord, thereby initiating central sensitization (13, 16).

Figure 1:
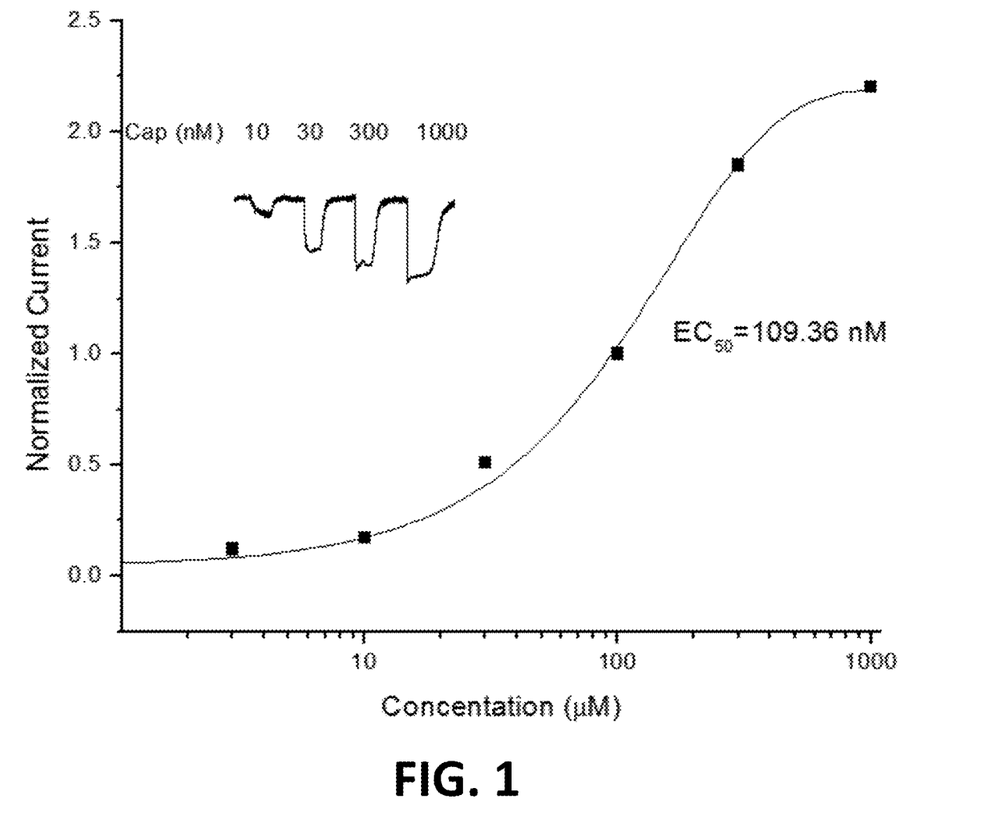
FIG. 1 is a dose-response curve of TRPV1 mediated currents induced by capsaicin.
Figure 2:
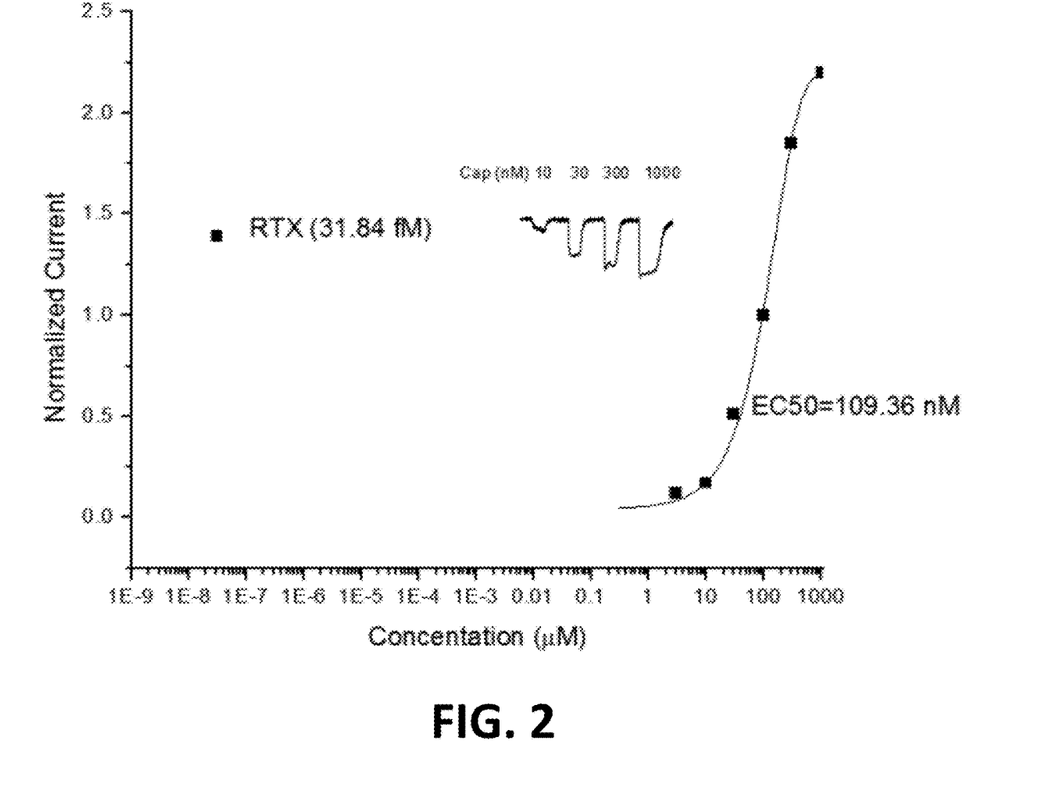
FIG. 2 is a dose-response curve to capsaicin shown along with RTX.
Figure 3:
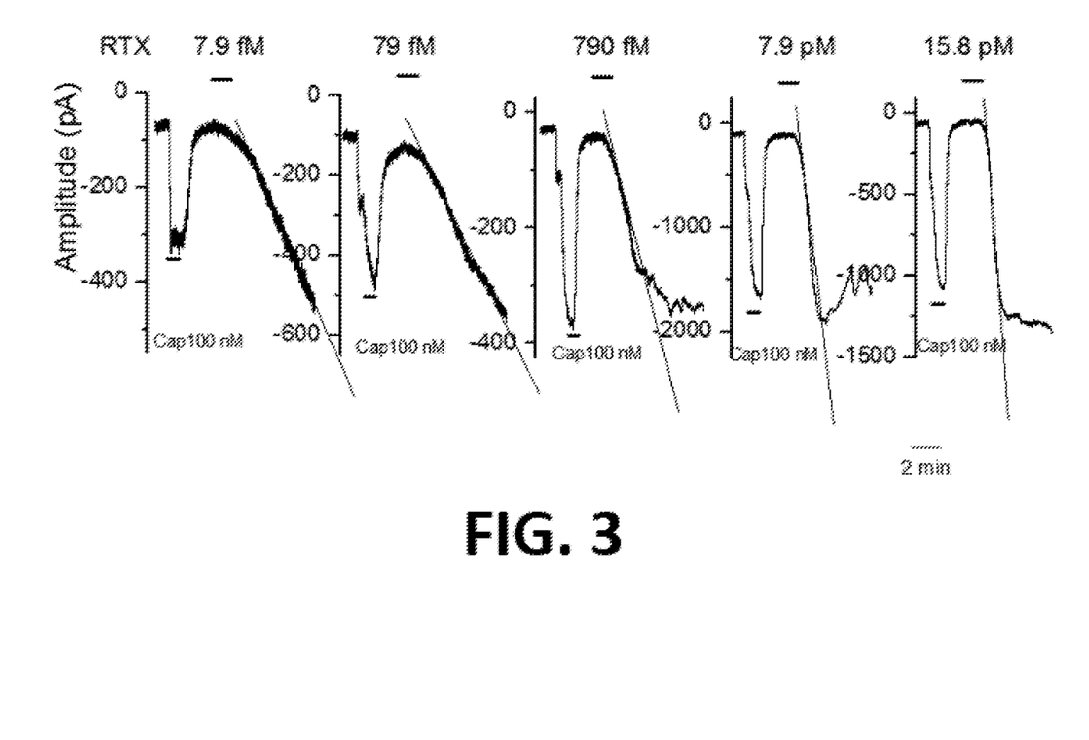
FIG. 3 reports that a response to capsaicin which is typically reversed by a washout, but RTX response cannot be reversed by washout.
Figure 4A:
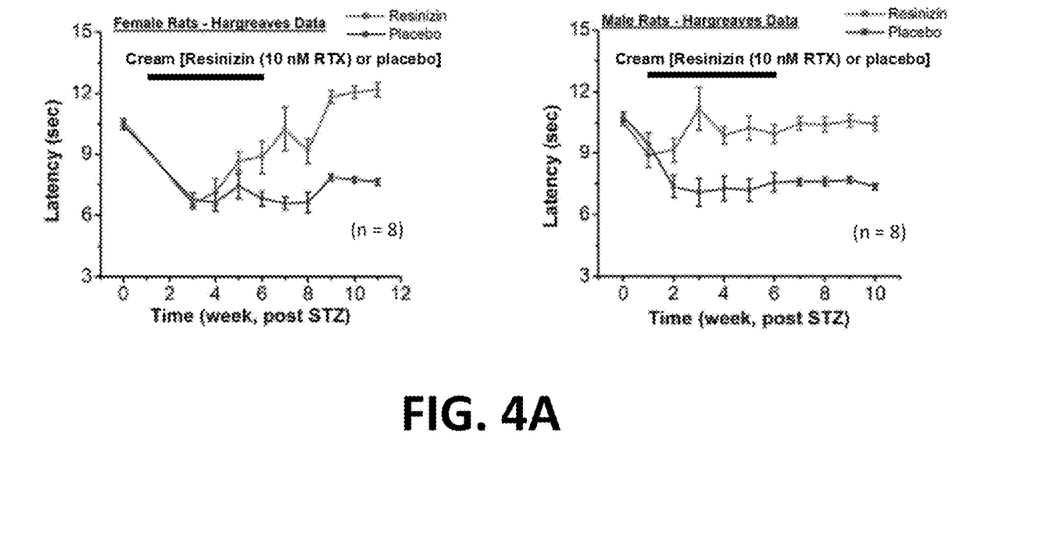
FIG. 4A reports effects of RTX cream on pain sensitivity in diabetic rats.
Figure 4B:
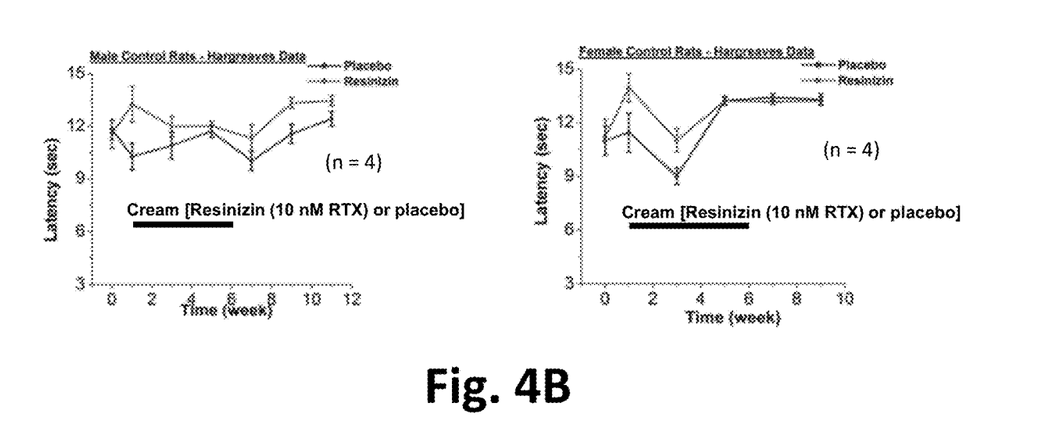
FIG. 4B reports effects of RTX cream on pain sensitivity in control rats.
Figure 4C:
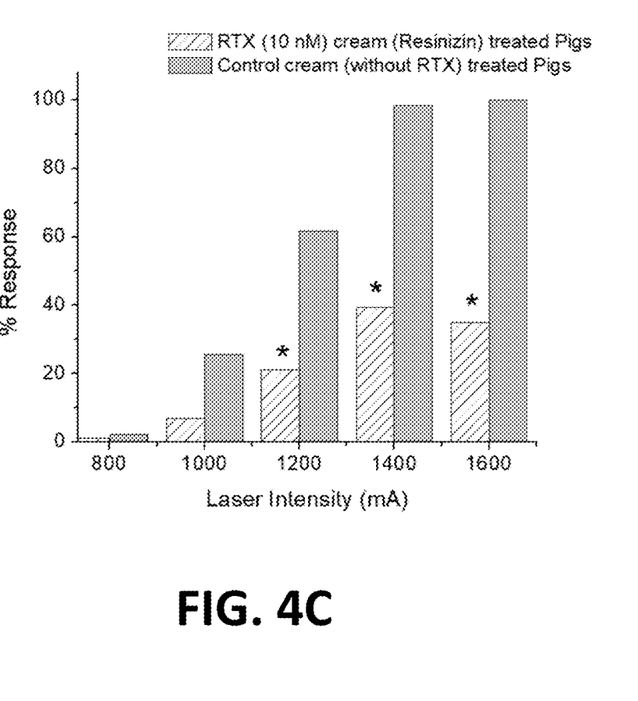
FIG. 4C reports effects of RTX cream on pain sensitivity in diabetic pigs.
Figure 5A:
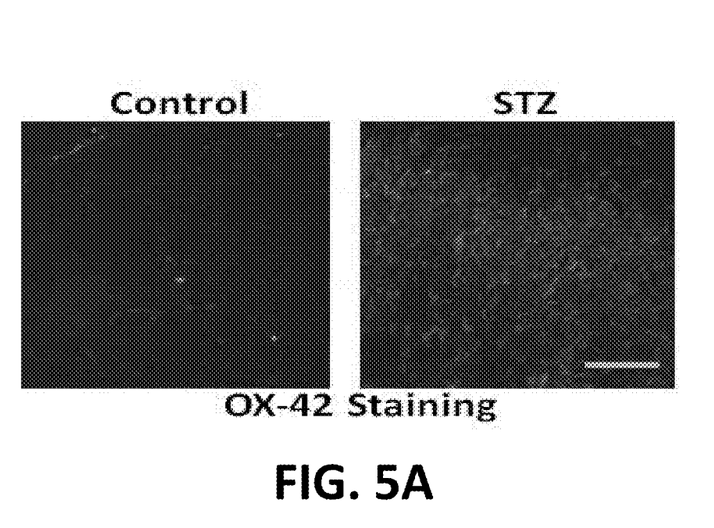
FIG. 5A are images of OX-42 staining.
Figure 5B:
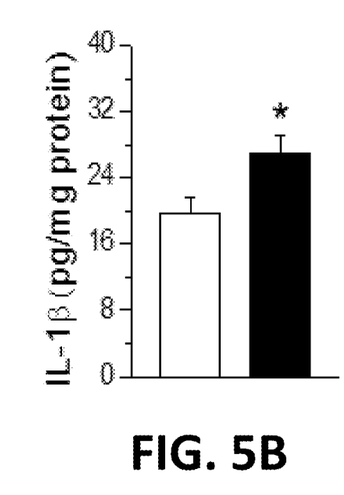
FIG. 5B reports an IL-10 increase in lumbar spinal cord tissue homogenates after the STZ treatment.
Figure 5C:
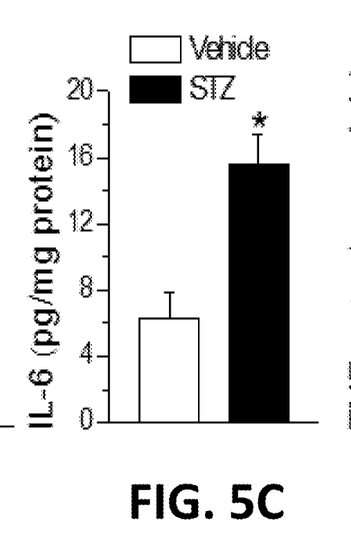
FIG. 5C reports an IL-6 increase in lumbar spinal cord tissue homogenates after the STZ treatment.
Figure 5D:
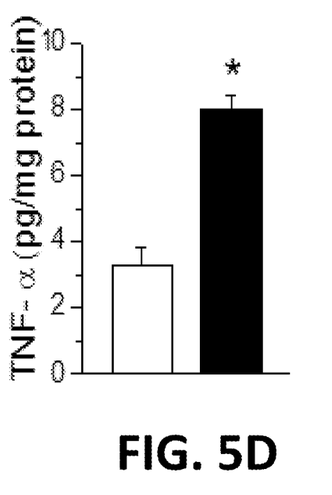
FIG. 5D reports an TNF-α increase in lumbar spinal cord tissue homogenates after the STZ treatment.

Higher levels of TRPV1-mediated CGRP release—the levels of which are reduced following RTX treatment—are expected in diabetic animals. T RPV1 protein levels, CGRP release and RTX binding are significantly higher in diabetic hyperalgesic animals. As a result of increased neuronal activity, microglia are activated which are associated with an increase in the proinflammatory mediators and a decrease in anti-inflammatory mediators (17, 18). FIGS. 5A, 5B, SC and SD report microglial activation after STZ treatment and the effect of STZ in spinal proinflammatory cytokine levels. FIG. 5A shows an OX-42 staining, while the bottom bar charts show IL-1β (FIG. 5B) IL-6 (FIG. 5C), and TNF-α (FIG. 5D) in lumbar spinal cord tissue homogenates, where asterisks * represent p<0.05. See also Bishnoi et al. 2011a and Bishnoi et al. 2011b.

As a result of central sensitization, increased synaptic activity is expected at the first sensory synapse between sensory neuron and second order neuron. Treatment with RTX cream prevents central sensitization and allodynia associated with DPN, although the frequency of events can vary dramatically from cell to cell. An increased synaptic activity can also modulate the firing pattern of the second order neuron and alter receptor expression. The RTX treatment is expected to result in ablation of TRPV1 expressing peripheral nerve terminals, which inhibits nociceptive transmission and prevent central sensitization and neuropathic pain.

Figure 6:
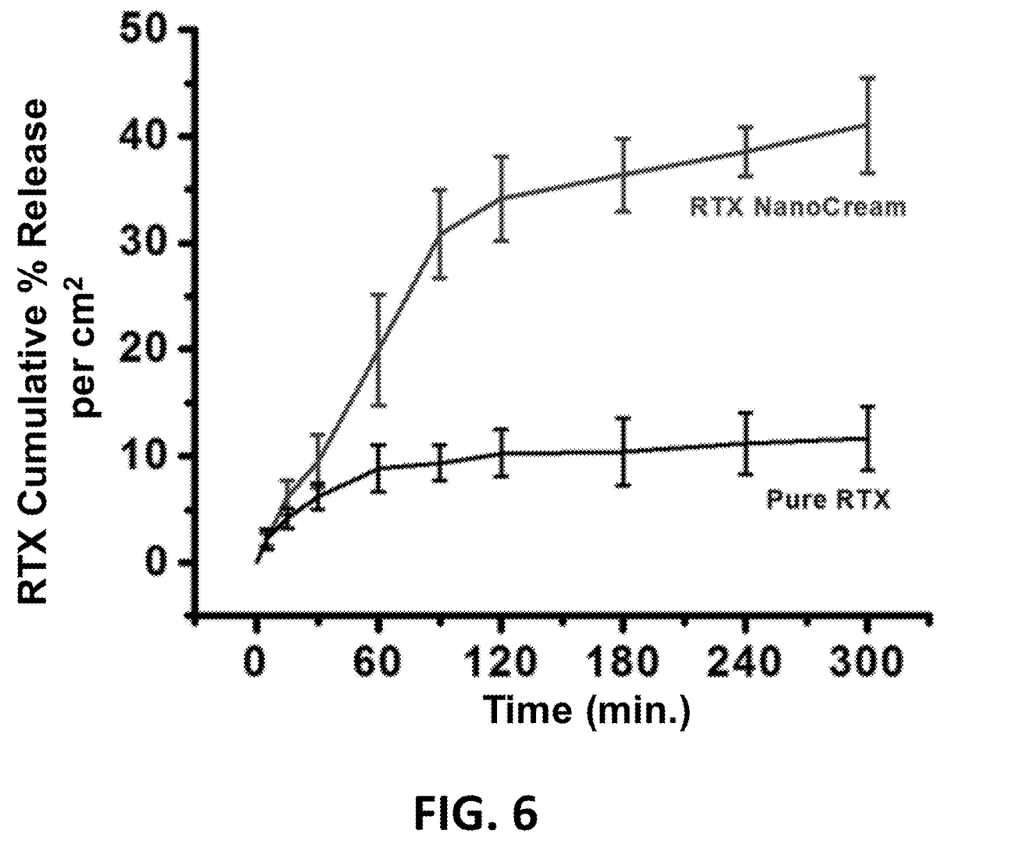
FIG. 6 is a comparative analysis in a cumulative percentage release of RTX versus a topical cream comprising PLGA-coated RTX nanoparticles.

Referring to FIG. 6, it reports a cumulative percentage release of resiniferatoxin from a cream composition comprising PLGA-coated RTX nanoparticles in comparison to a control composition in which resiniferatoxin is used in its pure form. As can be seen from FIG. 6, the cream composition comprising PLGA-coated RTX nanoparticles sustains stable and efficient release of resiniferatoxin.

TRPV1 antagonists can be effective in combating the peripheral effect of TRPV1 activation. Using a transgenic mouse model of diabetes and STZ-induced diabetes it has been shown that TRPV1 expression and function are increased and decreased in hyper or hypoalgesic phenotypes, respectively. The role of TRPV1 was confirmed by intrathecal administration of a potent TRPV1 agonist, RTX, that caused depolarization block of the TRPV1 expressing nerve terminals in the short-term and nerve terminal ablation in the long-term and reversed thermal hyperalgesia in STZ-induced diabetes. Intrathecal administration of RTX has been shown to be useful in acute and inflammatory pain conditions and is tested in a clinical trial for certain terminal cancer pain conditions.

Topical application of a composition comprising PLGA-coated RTX nanoparticles in DPN patients induces a dual effect, in that RTX not only targets TRPV1 in the peripheral terminals by causing depolarization block, but also prevents the neuronal activity-mediated increase in the expression of TRPV1 in the central terminals, which are involved in initiating/maintaining central sensitization.

Because of a high affinity of RTX on TRPV1 receptor, very low (picomolar) concentrations of RTX are expected to cause slow depolarization block and induce the expected antinociceptive effect in the short-term leading to nociceptive nerve terminal ablation in the long-term providing long lasting (6-8 weeks) pain relief. The present disclosure features an optimal, low concentration of RTX that can selectively cause depolarization block eventually leading to reversible nerve terminal ablation. This low-concentration approach is easy-to-use delivery vehicle (i.e. topical cream or other suitable topical formulation) and lack of pain upon application are expected to dramatically outweigh the possible need for more frequent application. The major advantage of the $_{PLGA}RTX^{NANO}$ topical composition vs. capsaicin analogues is that $_{PLGA}RTX^{NANO}$ can produce a long-lasting pain relief with a reduced frequency of application without any unpleasant burning sensation during application.

In further aspect, the present disclosure provides methods for preparing the PLGA-coated RTX nanoparticles according to this disclosure. Suitable methods include nanoprecipitation, salting out and emulsion evaporation.

One preferred method is nanoprecipitation. In this method, resiniferatoxin is dissolved in a suitable solvent. Suitable solvents include water-miscible solvents in which resiniferatoxin can be dissolved. One preferred solvent in ethanol. Various concentrations of resiniferatoxin can be used, including from 1 fM per liter to 10 μM per liter.

A poly(lactic-co-glycolic acid) (PLGA) co-polymer can be dissolved in an organic solvent, suitable solvents include dichloromethane. The PLGA can be used in different amounts. In some embodiments, from 0.001 to 2 parts by weight of resiniferatoxin can be used for 100 parts by weight of PLGA powder.

The two solutions are mixed together, and the resulting mixture is added dropwise to an aqueous solution with mixing. The aqueous solution comprises water a container, e.g. a beaker, test tube, etc. the aqueous solution may be kept at a particular pH and/or temperature in order to facilitate hardening of the nanoparticles. After the nanoprecipitation is completed, the resulting nanoparticles are collected by centrifugation and/or filtration. The resulting nanoparticles can be resuspended in a suitable solvent, e.g. water and may be further homogenized with a water bath sonicator and/or vortexer.

This nanoprecipitation protocol may be further adjusted as needed, in order to produce nanoparticles of the predetermined size and/or to obtain the nanoparticles with the preferred load (concentration) of resiniferatoxin.

Another method that can be used for obtaining the PLGA-coated RXT particles is evaporation. In this methods, resiniferatoxin and PLGA powder are dissolved in a suitable solvent, such as for example, as dichloromethane. The resulting mixture is mixed until the nanoparticles are formed. The mixture is then place in a rotavapor in order to evaporate the solvent.

This evaporation protocol may be further adjusted as needed, in order to produce nanoparticles of the predetermined size and/or to obtain the nanoparticles with the preferred load (concentration) of resiniferatoxin.

In further aspects, the present disclosure provides methods for preparing topic compositions according to this disclosure. In these methods, the PLGA-coated RTX nanoparticles obtained by the nanoprecipitation method or by any other method are mixed with one or more excipients. In some embodiments, the nanoparticles in an amount from 0.001% w/w to 99% w/w are mixed with one or more excipients.

The following non-limiting examples will add a person of skill further in their understanding of the present disclosure.

Example 1. Preparation of PLGA-Coated RTX ($_{PLGA}$RTX$^{NANO}$) Nanoparticles 100 mg of poly(lactic-co-glycolic acid) (PLGA) is weighed and placed in a test tube. 1 ml of dichloromethane (DCM) is added to the polymer. PLGA and DCM and ethanol can be obtained from Sigma. RTX in ethanol is added directly to the polymer solution and the tube is vortexed until the encapsulant is homogenously dispersed. RTX can be obtained from Tocris. Various suitable concentrations for RTX are provided in Table 1 below.

TABLE 1

Ingredients for 30 g of the Topical Cream Comprising $_{PLGA}$RTX$^{NANO}$ nanoparticles

| Ingredients | (concentrations equivalent to RTX) |
|---|---|
| $_{PLGA}$RTX$^{NANO}$ | 1 fM-628.7 fg/L |
| | 3 fM-1.8661 pg/L |
| | 0.1 μM-62.87 μg/L |
| | 0.3 μM-188.61 μg/L |
| | 1 μM-628.7 μg/L |
| | 3 μM-1.8661 mg/L |
| Ethanol | 5 ml |
| Dichloromethane | 10 ml |
| PLGA | 100 mg |

The nanoparticles are allowed to harden by adding in a beaker of distilled water, while stirring. The nanoparticles are centrifuged for 15 min at 17,000×g.

The supernatant is discarded. 15 ml of di$H_2O$ is added. A water bath sonicator and/or vortexer is used to completely resuspend the nanoparticles.

The nanoparticles can be characterized by using scanning electron microscopy (SEM).

Example 2. Preparation of Resiniferatoxin)($_{PLGA}RTX^{NANO}$ Cream

The PLGA-coated RTX)($_{PLGA}RTX^{NANO}$ nanoparticles can be prepared as described in Example 1. A quantity of $_{PLGA}RTX^{NANO}$ nanoparticles is mixed (see Table 1) with 15 grams of cream base in an electromagnetic jar. Various concentrations of PLGA-coated RTX) ($_{PLGA}RTX^{NANO}$ nanoparticles can be used as shown in Table 1.

A sufficient quantity of ActiveMax cream base is added to make 30 g of the RTX cream. The preparation is thoroughly mixed using an Unguator. The ointment is then milled to make a homogenous mixture of $_{PLGA}RTX^{NANO}$ cream. This ointment is transferred to tubes and sealed.

Example 3. Size Determination By Transmission Electron Microscopy

The samples are dried on TEM sample grid. A Gatan high-resolution 4 K×4 K digital camera and Gatan Digital Micrograph software (Pleasanton, Calif.) is used to image nanoparticles at high magnifications (40,000×) and 100,000× magnification to visualize and measure their size.

Example 4. X-Ray Diffractometry

X-ray powder diffraction pattern for the samples is measured at 25° C. on a Bruker SMART APEX II CCD area detector system equipped with a graphite monochromator and a Mo Ka fine-focus sealed tube operated at 1.5 kW power. About 5 mg of the each of samples is glued to a glass fiber using either paratone-N oil or epoxy and mounted on the goniometer. The samples are centered using the optical microscope of the diffractometer. The detector is placed at ca. 5.9 cm during the data collection. Four frames are collected using the Apex II software suite (APEX2 Software Suite V. 2.1-0, Bruker AXS: Madison, Wis., 2004)) with a scan width of 0.2° and an exposure time of 3 min per frame. The frames are then integrated using the Apex2 Pilot software program.

Example 5. In Vitro Dissolution and Pharmacokinetic Release Profiles of RTX from its PLGA-Coated Nano Formulation Hundred milligrams aliquots of $_{PLGA}RTX^{NANO}$ is placed in a dissolution basket paddle and suspended in 50 ml of isotonic pH 7.4 phosphate buffer solution (PBS) in a 6 well Vankel Dissolution system. The dissolution chamber is maintained at 37±0.5° C. At fixed time intervals, 5 ml of samples are taken out of the dissolution chamber and extracted three times with 5 ml of dichloromethane. The extraction solvent is evaporated and RTX residue is dissolved in DMSO, diluted in aqueous medium and the concentration of RTX is determined by UV-spectrophotometry (JASCO spectrophotometer) at 254 nm. The experiments are carried out in triplicate.

Example 6. Stability Analyses of RTX-Cream Nano Formulation

The physical stability of the cream formulation is determined in a temperature and humidity-controlled stability chamber at 40° C.+/−2° C./relative humidity 75%+/−5% for 4 months. The cream is evaluated for appearance, consistency, color, and odor of contents, assay, and diffusion. Microbial stability analyzes are also conducted. All tests are performed according to protocols specified in the United States Pharmacopeia.

Example 7. In-Vitro Analysis of a Topical Composition Comprising PLGA-Coated RTX Nanoparticles A cream of PLGA-coated RTX nanoparticles (100 nM) has been prepared by incorporating an ethanolic solution of RTX in to 5 g of cream base according to Examples 1 and 2. Either 5 mg of pure RTX drug or 350 mg of a cream formulation comprising PLGA-coated RTX nanoparticles of Example 2 (referred as the RTX nano-cream in the rest of this example) was placed and spread on a Strat-M Membrane (SKBM02560; EMD Millipore, USA).

The diffusion of the RTX nano-cream across the Strat-M membrane is predictive of diffusion in human skin. Accordingly, the RTX diffusion across membranes was investigated using a Franz diffusion cell.

The membrane was mounted between the donor and receptor compartment and either 5 mg of pure RTX or 350 mg of the RTX nano-cream was placed on the membrane surface inside the donor compartment. The receptor compartment was filled with a buffer solution pH 5.5 and stirred at 100 rpm. The buffer samples were collected from the receptor compartment at the end of 0, 5, 15, 30, 60, 90 and 120, 180, 240 and 300 min and analyzed for RTX concentration by measuring the absorbance at 210 nm in a JASCO V670 spectrophotometer. The cumulative amount of RTX diffusion over 5 hr. for each membrane was plotted against time. From these data, a calibration curve was plotted with the known concentrations of RTX ranging from 30 µg/L to 1 mg/L in pH 5.5 buffer. Experiments in triplicates were performed and analyzed. The results are reported in FIG. 6.

REFERENCES

1. Gaskin D J, Richard P. The economic costs of pain in the United States. J Pain. 2012 August; 13(8):715-24.
2. van Nooten F, Treur M, Pantiri K, Stoker M, Charokopou M. Capsaicin 8% Patch Versus Oral Neuropathic Pain Medications for the Treatment of Painful Diabetic Peripheral Neuropathy: A Systematic Literature Review and Network Meta-analysis. Clin Ther. 2017 April; 39(4):787-803.e18.
3. Boulton A J, Malik R A, Arezzo J C, Sosenko J M. Diabetic somatic neuropathies. Diabetes Care. 2004 June; 27(6):1458-86. Review.
4. Boulton A J, Vinik A I, Arezzo J C, Bril V, Feldman E L, Freeman R, Malik R A, Maser R E, Sosenko J M, Ziegler D; American Diabetes Association. Diabetic neuropathies: a statement by the American Diabetes Association. Diabetes Care. 2005 April; 28(4):956-62. Review.
5. Tesfaye S, Boulton A J, Dyck P J, Freeman R, Horowitz M, Kempler P, Lauria G, Malik R A, Spallone V, Vinik A, Bernardi L, Valensi P; Toronto Diabetic Neuropathy Expert Group. Diabetic neuropathies: update on definitions, diagnostic criteria, estimation of severity, and treatments. Diabetes Care. 2010 October; 33(10):2285-93. doi: 10.2337/dc10-1303. Review. Erratum in: Diabetes Care. 2010 December; 33(12):2725.
6. Veves A, Backonja M, Malik R A. Painful diabetic neuropathy: epidemiology, natural history, early diagnosis, and treatment options. Pain Med. 2008 September; 9(6):660-74. Review.
7. Boulton A J, Vinik A I, Arezzo J C, Bril V, Feldman E L, Freeman R, Malik R A, Maser R E, Sosenko J M, Ziegler D; American Diabetes Association. Diabetic neuropathies: a statement by the American Diabetes Association. Diabetes Care. 2005 April; 28(4):956-62. Review.
8. Alleman C J, Westerhout K Y, Hensen M, Chambers C, Stoker M, Long S, van Nooten F E. Humanistic and economic burden of painful diabetic peripheral neuropathy in Europe: A review of the literature. Diabetes Res Clin Pract. 2015 August; 109(2):215-25.
9. Capsaicin Study Group (1991): Treatment of painful diabetic neuropathy with topical capsaicin: a multicenter, double blind, vehicle-controlled study. *Arch Intern Med* 151:2225-2229.
10. Forst T, Pohlmann T, Kunt T, Goitom K, Schulz G, Lobig M, Engelbach M, Beyer J, Pfutzner A (2002) The influence of local capsaicin treatment on small nerve fiber function and neurovascular control in symptomatic diabetic neuropathy. *Acta Diabetologica* 39:1-6.
11. Gavva N R, Treanor J J, Garami A, Fang L, Surapaneni S, Akrami A, Alvarez F, Bak A, Darling M, Gore A, Jang G R, Kesslak J P, Ni L, Norman M H, Palluconi G, Rose M J, Salfi M, Tan E, Romanovsky A A, Banfield C, Davar G. Pharmacological blockade of the vanilloid receptor TRPV1 elicits marked hyperthermia in humans. Pain. 2008 May; 136(1-2): 202-10.
12. Gavva N R, Bannon A W, Surapaneni S, Hovland D N Jr, Lehto S G, Gore A, Juan T, Deng H, Han B, Klionsky L, Kuang R, Le A, Tamir R, Wang J, Youngblood B, Zhu D, Norman M H, Magal E, Treanor J J, Louis J C. The vanilloid receptor TRPV1 is tonically activated in vivo and involved in body temperature regulation. J Neurosci. 2007 Mar. 28; 27(13):3366-74.
13. Pabbidi R M, Yu S Q, Peng S, Khardori R, Pauza M E, Premkumar L S (2008a) Influence of TRPV1 on diabetes-induced alterations in thermal pain sensitivity. Mol Pain 1:4-9.
14. Premkumar L S, Ahern G P (2000) Induction of vanilloid receptor channel activity by protein kinase C. Nature 408: 985-990,
15. Raishinghani M, Pabbidi R M, Premkumar L S (2005) Activation of transient receptor potential vanilloid 1 (TRPV1) by resiniferatoxin. J Physiol 567: 771-786.
16. Pabbidi R M, Cao D S, Parihar A, Pauza M E, Premkumar L S (2008b) Direct role of streptozotocin in inducing thermal hyperalgesia by enhanced expression of TRPV1 in sensory neurons. Mol Pharmacol 73(3):995-1004.
17. Bishnoi M, Bosgraaf C A, Premkumar L S (2011a) Preservation of acute pain and efferent functions following intrathecal resiniferatoxin-induced analgesia in rats. J Pain. 2011a 12:991-1003.
18. Bishnoi M, Bosgraaf C A, Abooj M, Zhong L, Premkumar L S (2011b) Streptozotocin-induced early thermal hyperalgesia is independent of glycemic state of rats: role of transient receptor potential vanilloid 1(TRPV1) and inflammatory mediators. Mol Pain. 7:52.
19. Jeffry J A, Yu S Q, Sikand P, Parihar A, Evans M S, Premkumar L S (2009) Selective targeting of TRPV1 expressing sensory nerve terminals in the spinal cord for long lasting analgesia PLoS One 4:e7021.
20. Yu S, Premkumar L. S. (2015) Ablation and regeneration of peripheral and Central TRPV1 Expressing Nerve Terminals and the Consequence of Nociception. The Open Pain J. 8, 1-9.
21. Brown J D, Saeed M, Do L, Braz J, Basbaum A I, Iadarola M J, Wilson D M, DillonWP. C T-guided injection of a TRPV1 agonist around dorsal root ganglia decreases pain transmission in swine. Sci Transl Med. 2015 Sep. 16; 7(305):305ra145.
22. Brown D C, Agnello K, Iadarola M J. Intrathecal resiniferatoxin in a dog model: efficacy in bone cancer pain. Pain. 2015 June; 156(6):1018-24.
23. Salas M M, Clifford J L, Hayden J R, Iadarola M J, Averitt D L. LocalResiniferatoxin Induces Long-Lasting Analgesia in a Rat Model of Full Thickness Thermal Injury. Pain Med. 2016 Oct. 29.
24. Mitchell K, Bates B D, Keller J M, Lopez M, Scholl L, Navarro J, Madian N, Haspel G, Nemenov M I, Iadarola M J (2010). Ablation of rat TRPV1-expressing Adelta/C-fibers with resiniferatoxin: analysis of withdrawal behaviors, recovery of function and molecular correlates. Mol Pain 17; 6:94.
25. Mitchell K, Lebovitz E E, Keller J M, Mannes A J, Nemenov M I, Iadarola M J. (2014) Nociception and inflammatory hyperalgesia evaluated in rodents using infrared laser stimulation after Trpv1 gene knockout or resiniferatoxin lesion. Pain 155:733-45.
26. NCT00804154 (2008) Resiniferatoxin to Treat Severe Pain Associated with Advanced Cancer December 2008-December 2014. *National Institute of Dental and Craniofacial Research (NIDCR)*.

27. Iadarola M J, Mannes A J. The vanilloid agonist resiniferatoxin for interventional-based pain control. Curr Top Med Chem. 2011; 11(17):2171-9. Review.
28. Bril V, England J, Franklin G M, Backonja M, Cohen J, Del Toro D, Feldman E, Iverson D J, Perkins B, Russell J W, Zochodne D; American Academy of Neurology; American Association of Neuromuscular and Electrodiagnostic Medicine; American Academy of Physical Medicine and Rehabilitation. Evidence-based guideline: Treatment of painful diabetic neuropathy: report of the American Academy of Neurology, the American Association of Neuromuscular and Electrodiagnostic Medicine, and the American Academy of Physical Medicine and Rehabilitation. Neurology. 2011 May 17; 76(20):1758-65. doi: 10.1212/WNL.0b013e3182166ebe. Epub 2011 Apr. 11. Review. Erratum in: Neurology. 2011 Aug. 9; 77(6): 603.
29. Backonja M, Wallace M S, Blonsky E R, et al. NGX-4010 C116 StudyGroup. NGX-4010, a high-concentration capsaicin patch, for the treatment of postherpetic neuralgia: a randomised, double-blind study. Lancet Neurol. 2008; 7:1106-1112.
30. Irving G A, Backonj a M M, Dunteman E, et al. NGX-4010 C117 StudyGroup. Amulticenter, randomized, double-blind, controlled study of NGX-4010, a high-concen tration capsaicin patch, for the treatment of postherpetic neuralgia. PainMed. 2011; 12:99-109.
31. Simpson D M, Brown S, Tobias J, NGX-4010C107 Study Group. Controlled trial of high-concentration capsaicin patch for treatment of painful HIVneuropathy. Neurology. 2008; 70:2305-2313.
32. Haanpää M, Cruccu G, Nurmikko T J, et al. Capsaicin 8% patch versus oral pregabalin in patients with peripheral neuropathic pain. Eur J Pain. 2016; 20:316-328.
33. Simpson D M, Robinson-Papp J, Van J, et al. Capsaicin 8% patch in painful diabetic peripheralneuropathy: a randomised, double-blind, placebo-controlled study. J Pain. 2017; 18:42-53.
34. Jain Jain R A. The manufacturing techniques of various drug loaded biodegradable poly(lactide-co-glycolide) (PLGA) devices. Biomaterials. 2000 December; 21(23): 2475-90. Review.
35. Panyam J, Zhou W Z, Prabha S, Sahoo S K, Labhasetwar V. Rapid endo-lysosomal escape of poly(DL-lactide-co-glycolide) nanoparticles: implications for drug and gene delivery. FASEB J. 2002 August; 16(10):1217-26.
36. Baskaran M, Baskaran P, Arulsamy N, Thyagarajan B. Preparation and Evaluation of PLGACoated Capsaicin Magnetic Nanoparticles. Pharm Res. 2017 June; 34(6): 1255-1263. PubMedPMID: 28326459.
37. Jain Jain R A. The manufacturing techniques of various drug loaded biodegradable poly(lactide-co-glycolide) (PLGA) devices. Biomaterials. 2000 December; 21(23): 2475-90. Review.
38. Panyam J, Zhou W Z, Prabha S, Sahoo S K, Labhasetwar V. Rapid endo-lysosomal escape of poly(DL-lactide-co-glycolide) nanoparticles: implications for drug and gene delivery. FASEB J. 2002 August; 16(10):1217-26.
39. Baskaran M, Baskaran P, Arulsamy N, Thyagarajan B. Preparation and Evaluation of PLGACoated Capsaicin Magnetic Nanoparticles. Pharm Res. 2017 June; 34(6): 1255-1263. PubMedPMID: 28326459.

What is claimed is:

1. A nanoparticle comprising resiniferatoxin (RTX) encapsulated in a poly(lactic-co-glycolic acid) (PLGA) polymer for topical application, the nanoparticle having a size in the range from 5 nm to 100 nm, wherein the nanoparticle penetrates the transdermal skin barrier and wherein resiniferatoxin is loaded in the nanoparticle in a concentration ranging from 100 femtomoles (fM) to one micromole (µM).

2. A topical composition comprising the nanoparticle of claim 1 and one or more excipients.

3. The nanoparticle of claim 1, wherein the ratio of lactic acid to glycolic acid is 25/75; 50/50; or 75/25.

4. The nanoparticle of claim 1, wherein the nanoparticle is PEGylated.

5. The nanoparticle of claim 1, wherein the nanoparticle further comprises one or more of the following: an anti-inflammatory drug, an antibiotic, an anti-viral drug, an anti-fungal drug, a vitamin, vitamin E, vitamin D or an analgesic.

6. The composition of claim 2, wherein the composition further comprises one or more of the following: an anti-inflammatory drug, an antibiotic, an anti-viral drug, an anti-fungal drug, or an analgesic.

7. The composition of claim 2, wherein the composition is in a form of a cream, ointment, liniment, lotion, gel, collodion, paste, patch, tape, solution, spray, foam or an injectable solution.

8. The composition of claim 2, wherein the composition comprises alcohol, polyethylene glycol (PEG), glycerin, lecithin, shea butter, coconut oil, ascorbyl palmitate, xanthan gum and/or disodium ethylenediaminetetraacetic acid (EDTA).

9. The composition of claim 8, wherein the alcohol is cetearyl alcohol.

10. The composition of claim 2, wherein the composition further comprises a nonsteroidal anti-inflammatory drug and/or vitamin E and/or vitamin D.

11. A method of using the composition of claim 2 in a diabetic patient whose symptoms include diabetic peripheral neuropathy or the subject has one or more of the following diseases and/or conditions: peripheral neuropathy, diabetic peripheral neuropathy, herpes, shingles, arthritis, osteoarthritis, rheumatoid arthritis, a swollen joint, muscle pain, muscle soureness, muscle stiffness, muscle crumps, an insect bite, skin injury, skin burn, back pain, low back pain, knee pain, elbow pain, shoulder tension, or a joint injury.

12. The method of claim 11, wherein the composition is applied at least once a month or at least once a week.

13. A method for making the nanoparticle of claim 1, the method comprising:
   a) dissolving resiniferatoxin in a first solvent and obtaining a first solution, wherein the first solvent is water-miscible;
   b) dissolving a poly(lactic-co-glycolic acid) (PLGA) polymer powder in a second solvent, and obtaining a second solution;
   c) mixing the first solution together with the second solution, and obtaining a mixture;
   d) adding the mixture dropwise to an aqueous solution with mixing, and thereby forming the nanoparticles; and
   e) collecting the nanoparticles by one or more of centrifugation and/or filtration.

14. The method of claim 13, wherein the method is further characterized by one or more of the following features:
   i) a concentration of resiniferatoxin in the first solution is in the range from 1fM per liter to 10 µM per liter;
   ii) the first solvent contains ethanol;

iii) the second solvent contains dichloromethane; and/or
iv) from 0.001 to 2 parts by weight of resiniferatoxin can be used for 100 parts by weight of the PLGA powder.

\* \* \* \* \*